United States Patent

Verbitsky et al.

(10) Patent No.: US 9,572,955 B2
(45) Date of Patent: Feb. 21, 2017

(54) CATHETER-TO-EXTENSION TUBE ASSEMBLY AND METHOD OF MAKING SAME

(75) Inventors: Gary Verbitsky, Emmaus, PA (US); Mahase Nardeo, Collegeville, PA (US)

(73) Assignee: Medical Components, Inc., Harleysville, PA (US)

(*) Notice: Subject to any disclaimer, the term of this patent is extended or adjusted under 35 U.S.C. 154(b) by 982 days.

(21) Appl. No.: 12/331,997

(22) Filed: Dec. 10, 2008

(65) Prior Publication Data

US 2009/0157052 A1 Jun. 18, 2009

Related U.S. Application Data

(60) Provisional application No. 61/007,387, filed on Dec. 12, 2007.

(51) Int. Cl.
*A61M 25/00* (2006.01)
*B29C 45/14* (2006.01)
*B29K 75/00* (2006.01)
*B29L 31/00* (2006.01)

(52) U.S. Cl.
CPC .... *A61M 25/0097* (2013.01); *B29C 45/14467* (2013.01); *A61M 25/0045* (2013.01); *B29K 2075/00* (2013.01); *B29L 2031/7542* (2013.01)

(58) Field of Classification Search
CPC ............ A61M 25/0097; A61M 25/0014; A61M 39/10; A61M 2039/1077; A61M 25/0009; A61M 25/0905; A61M 16/0875; A61M 2025/0034; A61M 2025/004; A61M 25/0026; A61M 25/0028; A61M 25/0071; A61M 39/105; A61M 25/0045; B29C 45/14467; B29K 2075/00; B29L 2031/7542
USPC ............... 604/533–535, 508; 285/124.4
See application file for complete search history.

(56) References Cited

U.S. PATENT DOCUMENTS

| | | | |
|---|---|---|---|
| 4,037,599 A | 7/1977 | Raulerson | |
| 4,592,749 A * | 6/1986 | Ebling et al. | 604/533 |
| 6,719,330 B2 * | 4/2004 | Brown et al. | 285/242 |
| 2004/0183305 A1 * | 9/2004 | Fisher | 285/419 |
| 2004/0243103 A1 * | 12/2004 | King et al. | 604/533 |
| 2005/0080398 A1 | 4/2005 | Markel et al. | |
| 2005/0148929 A1 * | 7/2005 | Gingles | 604/95.04 |
| 2005/0209581 A1 * | 9/2005 | Butts et al. | 604/523 |
| 2007/0016167 A1 * | 1/2007 | Smith et al. | 604/533 |
| 2007/0060866 A1 | 3/2007 | Raulerson et al. | |
| 2007/0106261 A1 * | 5/2007 | DiMatteo et al. | 604/523 |
| 2007/0260221 A1 | 11/2007 | Chesnin | |
| 2009/0005741 A1 | 1/2009 | Martin et al. | |

* cited by examiner

*Primary Examiner* — Bhisma Mehta
*Assistant Examiner* — Brandy S Lee
(74) *Attorney, Agent, or Firm* — Fox Rothschild LLP

(57) ABSTRACT

A catheter assembly (10) having a catheter (12) with lumens (20a, 20b), extension tubes (14a, 14b) and a hub (16). Distal ends (36) of the extension tubes and the proximal end (24) of the catheter are secured in and to the hub. Fittings (50) are first affixed in the distal ends of the extension tubes and have annular collars (56) that are embedded in the hub when the hub is molded over the distal ends of the extension tubes during manufacturing. An array of annular barbs (60) secure the cylindrical portion (52) of each fitting in the respective extension tube distal end (36).

18 Claims, 2 Drawing Sheets

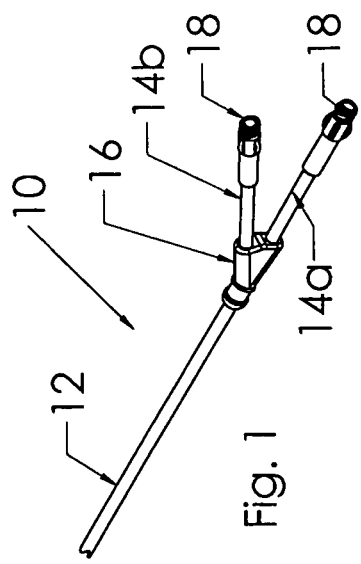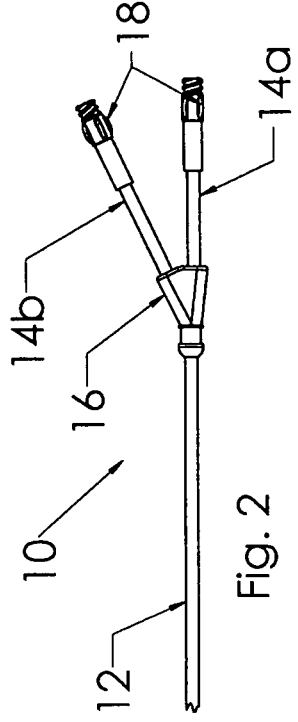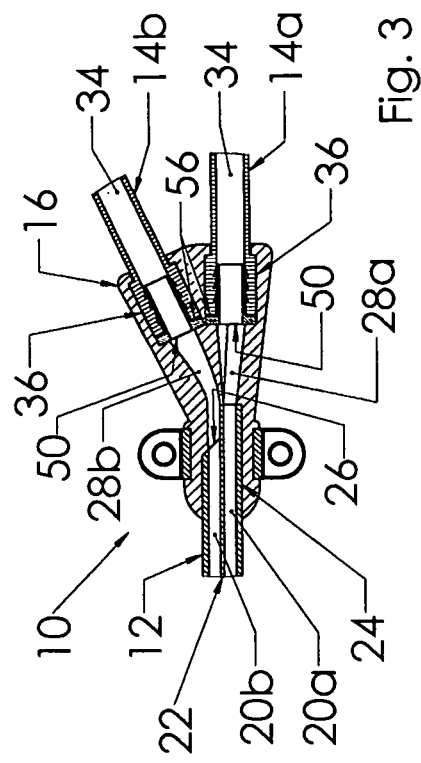

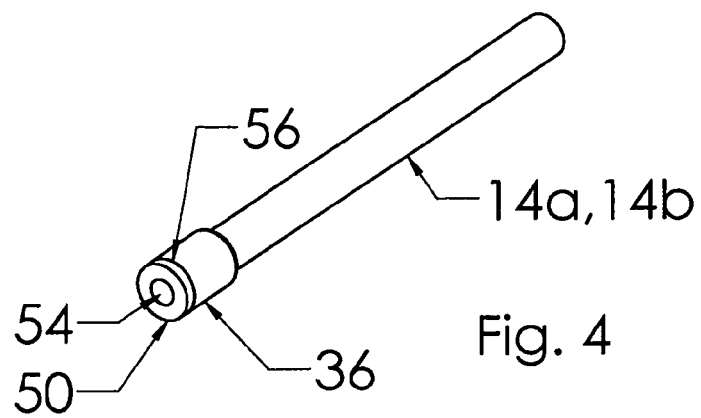
Fig. 4
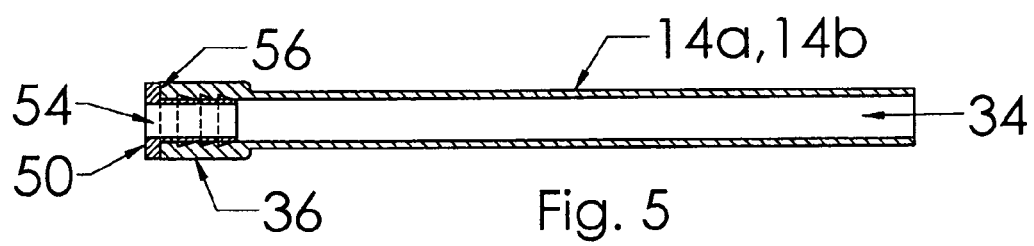
Fig. 5
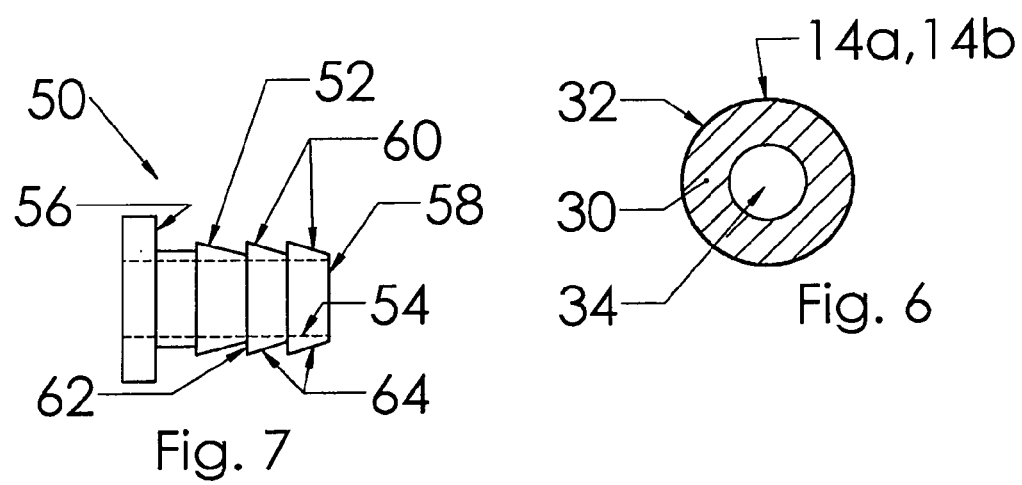
Fig. 7
Fig. 6

CATHETER-TO-EXTENSION TUBE ASSEMBLY AND METHOD OF MAKING SAME

CROSS-REFERENCE TO RELATED APPLICATIONS

This application claims priority from U.S. Provisional Application Ser. No. 61/007,387, filed Dec. 12, 2007.

FIELD OF THE INVENTION

This relates to the field of medical devices, and more particularly to catheter assemblies.

BACKGROUND OF THE INVENTION

Vascular catheters having extension tubes joined to their proximal ends are known, with catheters conventionally being made of either silicone or polyurethane while the extension tubes are polyurethane or polymers other than silicone. One manner of connecting an extension tube to a catheter lumen is to provide complementary luer fittings on both the proximal catheter end and the distal tube end, for removable connections. Another manner of connection, especially for use on multi-lumen catheters, is to provide a hub component that is affixed to the proximal end of the catheter and to the distal ends of one or more extension tubes associated with respective lumens of the catheter; the hub provides a channel or passageway establishing fluid communication between each extension tube and a respective lumen of the catheter, defining a catheter assembly. Commonly, the hub is insert molded of polyurethane onto the respective catheter and extension tube ends with the use of mandrels that define the channels of the hub during molding. Use of such assemblies is well known for hemodialysis and for infusion of medication into or drawing of blood from a patient, or both.

Molding of a hub onto a proximal end of a multi-lumen catheter simultaneously with molding it onto the distal ends of a plurality of extension tubes associated with the catheter lumens, is known. One such molding process is disclosed in U.S. Patent Publication No. 2005/0080398, which disclosure is incorporated hereinto by reference, including the use of mandrels extending from within the extension tube passageways and into the associated lumens of the catheter at the proximal ends thereof. The mandrel portions extending between the extension tube distal ends and the catheter proximal end define passageways through the hub body formed within a hub mold to surround end portions of the extension tubes and the catheter and seal with outer surfaces thereof, which hub passageways define fluid communication between the extension tube passageways and the respective lumens.

It is desired to provide a manner of connecting a catheter lumen to a respective extension tube where the extension tube may be made at least partly of silicone.

BRIEF SUMMARY OF THE INVENTION

Briefly, the present invention provides a method of manufacturing a catheter assembly that includes a hub and at least one extension tube that is at least partly of silicone. A generally cylindrical fitting has a passageway therethrough, an annular collar at one end, and at least one annular barb therearound having its angled surface facing away from the collar and a substantially perpendicular surface facing the collar. The diameter of each at least one barb is larger than the inner diameter of the passageway of the extension tube. The fitting is first inserted into a distal end of the extension tube. Preferably, an array of at least two or three annular barbs are provided on the fitting, and the angles thereof are preferably small for ease of insertion into the extension tube distal end and for minimizing the damage to the extension tube, since the fitting expands the extension tube inner diameter during insertion. The barbs will act to prevent movement of the extension tube relatively away from the fitting.

The distal end of the extension tube, including the fitting affixed thereinto, is placed into a mold cavity in which the hub will be molded, and the catheter proximal end is also placed into the mold cavity, with mandrels extending through the extension tube (and fitting) and the catheter such that portions of the mandrels also extend through the mold cavity. The hub is then molded therearound, after which the mandrels are removed from the molded assembly. In the completed assembly, the fitting will secure the extension tube to the proximal end of the hub by reason of the annular collar surrounded by molded material of the hub, especially proximally of the collar. A plurality of such extension tubes with fittings would be simultaneously molded and embedded within a hub in the same fashion, for a multi-lumen catheter.

The extension tube comprises silicone and preferably a thin outer layer is provided thereover of polyurethane. The silicone has better shape memory to resist deformation by Roberts clamps and the like, and also has greater lubricity facilitating the passing therethrough of a guide wire, during insertion of the catheter into a patient, but has a disadvantage of less-than-optimum adhesion to and sealing with the polyurethane material of the hub during insert molding thereof. The thin outer layer of polyurethane provides for sealing with the molded hub, while the fitting of the present invention assures that the extension tube is firmly secured to the hub.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 1 and 2 are an isometric view and a longitudinal cross-sectional view, respectively, of a catheter assembly that includes two extension tubes joined to a dual lumen catheter via a hub;

FIG. 3 is an enlarged cross-sectional view of the hub showing the passageways establishing fluid communication of the extension tubes with respective passageways of the two lumens of the catheter, and also shows the fittings of the present invention;

FIGS. 4 to 6 are isometric, longitudinal cross-sectional and cross-sectional views, respectively, of an extension tube of FIGS. 1 to 3; and FIG. 7 is an elevation view of a fitting of FIGS. 2 to 5.

DETAILED DESCRIPTION OF THE INVENTION

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Catheter assembly 10 in FIGS. 1 and 2 includes a dual lumen catheter 12, a pair of extension tubes 14a, 14b and a hub 16, with luer fittings 18 affixed to proximal ends of the extension tubes. Each extension tube is in fluid communication with a respective lumen of catheter 12, which lumens 20a, 20b are of a conventional D-shaped cross-section where the lumens are separated by an internal wall or septum 22, seen in FIG. 3. Lumen 20a is aligned with a corresponding passageway 28a of hub 16 along a coincident axis that is also the axis of the respective extension tube 14a, while lumen 20b is foreshortened at 26 to enable an angled passageway 28b of the hub to have a short portion that is coincident with the longitudinal axis of the lumen 20b while the angled passageway portion is coincident with the axis of extension tube 14b.

FIG. 3 also shows fittings 50 secured to the distal ends of each extension tube 14a, 14b, each of the fittings including an enlargement such as an annular collar 56 at the end face of the respective extension tube that protrudes radially beyond the outer diameter of the extension tube to establish a stop section securing the fitting and therefore the extension tube to the hub 16 upon insert molding of the hub to the distal ends of the extension tubes and the proximal end 24 of the catheter. FIG. 3 also depicts that the fitting having a distal enlargement embedded within the hub proximal end portion distally of a portion of the hub is smaller in dimension than the distal enlargement of the fitting.

FIGS. 4 and 5 illustrate an extension tube 14a, 14b having a fitting 50 secured thereto, the fitting having a tubular proximal section 52 disposed within the passageway 34 of the extension tube and having a passageway 54 in fluid communication with passageway 34. The fitting further includes a distal enlargement such as annular collar 56, with annular collar 56 positioned adjacent to the end face of the extension tube and protruding radially outwardly to a diameter greater than the outer diameter of the extension tube even after the tube's distal end portion 36 has been expanded to fit over the fitting. The annular collar assures that the extension tube with its fitting remains mechanically anchored within and assuredly secured to the hub. Best seen in FIG. 7, fitting 50 extends to a proximal end 58 and is provided with at least one, preferably two or three barbs 60 therealong protruding radially outwardly. Fitting passageway 54 extending therethrough having an inner diameter matching that of passageway 34 of the extension tube. Barbs 60 secure the fitting in the distal end of extension tube 14a, 14b when fitting 50 is pressed into the distal end of the tube, with sharply angled barb faces 62 that are directed distally to prevent the extension tube from moving proximally from the fitting thereafter while gently sloping proximal faces 64 facilitate insertion of the fitting into the extension tube. The extension tube is expanded slightly at distal end 36 by the fitting 50, and grips the fitting tightly, after the fitting is pressed thereinto.

As shown in FIG. 6, preferably the extension tube comprises an inner layer 30 of substantial thickness of silicone, and a thin, outer layer 32 of polyurethane. The inner layer of silicone provides the advantages of better shape memory for the extension tube to consistently retain its intended undeformed cylindrical inner diameter even after repeatedly being clamped and unclamped by a Roberts clamp (not shown). The outer layer of polyurethane assures sealing with the polyurethane hub material therearound by fusing therewith.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A catheter assembly comprising:
   a catheter having at least one lumen extending from a distal end to a proximal end;
   an extension tube associated with each at least one lumen and having a distal end and a proximal end, each extension tube comprising at least a layer of silicone; and
   a hub having a distal end portion associated with the catheter proximal end, and having a proximal end portion with which each extension tube is associated, the hub physically joining the catheter and each at least one extension tube and including at least one passageway, each passageway establishing fluid communication between a respective catheter lumen and a respective extension tube,
   wherein each extension tube distal end is secured within and to the hub by a fitting secured to the extension tube distal end, the fitting being disposed within a proximal end portion of a respective hub passageway, and the fitting having a distal enlargement embedded within the hub proximal end portion distally of a portion of the hub that is smaller in dimension than the distal enlargement of the fitting and the fitting having at least one annular barb disposed on a fitting section within the extension tube distal end that secures the fitting to the extension tube.

2. The catheter assembly of claim 1, wherein the distal enlargement is an annular collar.

3. The catheter assembly of claim 1, wherein the fitting includes a plurality of annular barbs disposed on the fitting section.

4. The catheter assembly of claim 1, wherein each extension tube includes an outer layer of a material substantially identical to material from which the hub is composed.

5. The catheter assembly of claim 4, wherein the material of the hub and the outer layer is polyurethane.

6. The catheter assembly of claim 1, wherein the hub is molded around the proximal end of the catheter and the distal end of each extension tube including the fitting affixed thereto.

7. The catheter assembly of claim 1, wherein each fitting is sized to enlarge the distal end of the associated extension tube upon being inserted thereinto.

8. The catheter assembly of claim 1, wherein the catheter has two lumens and the assembly includes two said extension tubes respectively associated with the two lumens, and two said fittings each secured to a respective extension tube distal end.

9. The catheter assembly of claim 1, wherein each extension tube distal end is secured within and to the hub by a respective fitting.

10. A method of making a catheter assembly having a catheter with a proximal end and at least one lumen, an extension tube associated with each lumen of the catheter and having a distal end, and a hub joining the catheter proximal end to the distal end of each extension tube, comprising:
  providing a catheter having at least one lumen and a proximal end;
  providing an extension tube associated with each at least one catheter lumen and each having a distal end;
  inserting into and securing to the distal end of each extension tube, a fitting wherein the fitting has an enlargement at its distal end sized to enlarge the distal end of the extension tube upon being inserted thereinto; and
  molding a hub about the proximal end of the catheter, and about the distal ends of the extension tubes inclusive of their fittings,
  whereby the enlargement of each fitting is embedded and anchored within a proximal end portion of the hub and securing the respective extension tube to the hub.

11. The method of claim 10, wherein the extension tube is of silicone and having an outer layer of material similar to material from which the hub is composed, forming a seal therebetween.

12. The method of claim 11, wherein the material of the hub and the outer layer is polyurethane.

13. The method of claim 10, wherein each extension tube distal end is secured within and to the hub by a respective fitting.

14. A catheter assembly comprising:
  a catheter having two lumens extending from a distal end to a proximal end of the catheter;
  two extension tubes, each being associated with a respective lumen and having a distal end and a proximal end; and
  a hub physically joining the catheter and the two extension tubes and establishing fluid communication between each catheter lumen and a respective extension tube, the hub being molded around the catheter proximal end and the distal ends of the two extension tubes,
  wherein each extension tube distal end is secured to and within the hub by a fitting secured to the extension tube distal end, each fitting having a distal enlargement embedded within a proximal end portion of the hub, distally of a hub proximal end portion adjacent the hub proximal end that is smaller in dimension than the distal enlargement and wherein each fitting is sized to enlarge the distal end of the associated extension tube upon being inserted thereinto.

15. The catheter assembly of claim 14, wherein each extension tube comprises at least a layer of silicone.

16. The catheter assembly of claim 14, wherein each extension tube includes an outer layer of a material substantially identical to material from which the hub is composed.

17. The catheter assembly of claim 16, wherein the material of the hub and the outer layer is polyurethane.

18. The catheter assembly of claim 16, wherein each extension tube distal end is secured within and to the hub by a respective fitting.

* * * * *